(12) United States Patent
Yoo et al.

(10) Patent No.: US 6,358,761 B1
(45) Date of Patent: Mar. 19, 2002

(54) SILICON MONITOR FOR DETECTION OF $H_2O_2$ IN ACID BATH

(75) Inventors: Hui-Ju Yoo; Szu-An Wu, both of Hsin-Chu; Cheng-Kun Lin, Taipei; Shiow-Jye Jenq, Hsin-Chu, all of (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 0 days.

(21) Appl. No.: 09/396,521

(22) Filed: Sep. 15, 1999

(51) Int. Cl.[7] .............................................. H01L 21/265
(52) U.S. Cl. ........................ 438/14; 438/514; 438/756
(58) Field of Search ........................ 438/14, 514, 770, 438/906, 745, 756, 753; 422/68.1; 156/345, 627

(56) References Cited

U.S. PATENT DOCUMENTS

| | | | |
|---|---|---|---|
| 4,668,330 A | 5/1987 | Golden | 156/601 |
| 5,338,390 A | 8/1994 | Barbee et al. | 156/627 |
| 5,418,172 A | 5/1995 | Falster et al. | 437/8 |
| 5,430,318 A | * 7/1995 | Hsu | 257/370 |
| 5,439,569 A | 8/1995 | Carpio | 204/153.1 |
| 5,573,623 A | 11/1996 | Barbee et al. | 156/345 |

FOREIGN PATENT DOCUMENTS

| | | | |
|---|---|---|---|
| JP | 61148865 | * 7/1986 | 438/586 |
| JP | 08086725 | * 9/1994 | |

* cited by examiner

*Primary Examiner*—Savitri Mulpuri
(74) *Attorney, Agent, or Firm*—George O. Saile; Stephen B. Ackerman; Alek Szecoy

(57) ABSTRACT

A method and means for detection of oxidizing contamination in acid etching baths employed to etch silicon oxide layers from silicon substrates employed in silicon integrated circuit microelectronics fabrications. There is provided a silicon substrate having within a doped region formed employing ion implantation. The silicon substrate is immersed within a buffered oxide etch (BOE) acid bath, wherein the presence of an oxidizing contaminant correlates with an increase in the resistance of the doped region upon the removal of any silicon oxide layer on the silicon surface.

8 Claims, 2 Drawing Sheets

SILICON MONITOR FOR DETECTION OF $H_2O_2$ IN ACID BATH

BACKGROUND OF THE INVENTION

1. Field of the Invention

The invention relates to the field of manufacture of microelectronics fabrications. More particularly the invention relates to the field of monitoring and detecting contamination in silicon integrated circuit microelectronics fabrication processes.

2. Description of the Related Art

Fabrication of silicon integrated circuit microelectronics devices requires the employment of various chemical processes. A typical microelectronics fabrication is composed of many different materials laminated together, some of which are patterned employing masking techniques and subtractive etching methods employing both wet and dry chemical environments. Of particular interest are chemical systems for etching silicon containing dielectric layers in a controlled fashion. Silicon oxide layers, for example, may often be required to be removed by etching from silicon substrates at a known rate and without deleterious effects on the silicon substrate.

One of the principal factors involved in obtaining the proper etch rate of a reagent is the presence or absence of certain impurities. Hence a particular concern is the assurance of purity of reagents. In the case of etching silicon oxide layers on silicon substrates, the etching performance of a particular acid etch bath known as buffered oxide etch (BOE) is greatly affected by the reagent concentration and temperature. Although satisfactory performance is obtained from BOE acid etch bath when proper concentration and temperature are maintained, the use of BOE acid etch bath for etch removal of silicon oxide layers from silicon substrates before metallization is not without problems.

Etching baths are constantly monitored to assure that they are functioning properly and providing the required etch rate. It is a common practice to treat BOE acid etch baths with hydrogen peroxide ($H_2O_2$) to control certain impurity substances which may cause deviations from the specified etch rate. Since hydrogen peroxide may act as an oxidizing agent in acid baths, any excess of this material may itself act as a particular contaminant which could result in yield loss of microelectronics fabrications at Wafer Acceptance Test (WAT) final test. A lengthy period of time is thus required to determine if contamination was present by yield loss data, due to the large number of processes. Some form of current real-time process monitoring is desirable to determine if oxidizing contamination by substances such as, for example, hydrogen peroxide has occurred in the BOE acid etch bath.

It is therefore towards the goal of assuring the freedom of acid etching baths employed within microelectronics fabrication processes from impurities such as oxidizing substances that the present invention is particularly directed.

Various methods and devices have been proposed to monitor the condition of manufacturing equipment and chemical reagent solutions employed in microelectronics fabrication with respect to contamination by deleterious substances.

For example, Golden, in U.S. Pat. No. 4,668,330, discloses a method for employing a test wafer to monitor furnace contamination from heavy metal impurities. The method employs exposure of silicon substrates whose degree of oxygen induced stacking faults is a measure of the extent of contamination by heavy metal elements to the furnace environment. The observation of stacking faults by selective etching of the monitor wafers.

Further, Falster et al., in U.S. Pat. No. 5,418,172, disclose a method employing a monitor wafer to measure transition metals contamination in or on equipment and fluids employed in fabrication or handling of silicon wafers employed in silicon integrated circuits. The method employs the exposure of monitor silicon wafers which have a measured minority carrier lifetime of greater than about 250 microseconds to a given process employing equipment or fluids. As part of or in addition to the process, the monitor wafer is exposed to a temperature of at least 600 degrees centigrade and the minority carrier lifetime re-measured to ascertain the amount of transition metals picked up by the monitor silicon wafer.

Still further, Carpio, in U.S. Pat. No. 5,439,569, discloses a method for measuring $H_2O_2$ concentration in chemical baths used for semiconductor processing. The method employs potentiometric and amperometric measurements whose values are related to the amounts of ammonia or water present in the hydrogen peroxide baths.

Finally, Barbee et al., in U.S. Pat. No. 5,573,623 and U.S. Pat. No. 5,338,390, disclose a method employing contactless electrodes to determine the end point of etching or other similar process where an abrupt phase change accompanies the completion of the process. The electrodes are toroidal coils positioned adjacent to the objects being processed, and are supplied with an AC signal which is monitored. When the process being monitored is completed, there is an abrupt change in the transmission characteristics of the AC signal which is sensed as the end point of the process.

Desirable in the art of silicon integrated circuit microelectronics fabrication are additional methods for monitoring the amount of contamination present in acid baths for etching silicon oxide layers on silicon substrates.

It is towards this goal that the present invention is generally and specifically directed.

SUMMARY OF THE INVENTION

A first object of the present invention is to provide a method to detect the presence of contamination in a reagent solution employed in the manufacture of silicon microelectronics fabrications.

A second object of the present invention is to provide as a means in accord with the first object of the present invention a monitor silicon substrate to implement the detection and monitoring of contamination in an buffered oxide etch (BOE) acid bath employed to etch silicon oxide layers formed upon silicon substrates in the manufacture of silicon integrated circuit microelectronics fabrications.

A third object of the present invention is to provide a method in accord with the first object of the present invention and/or the second object of the present invention, to fabricate a monitor silicon substrate employed as a means to detect and monitor the concentration of oxidizing contamination in a 50:1 BOE acid etch bath employed to etch silicon oxide layers formed upon silicon substrates in the manufacture of silicon integrated circuit microelectronics fabrications.

A fourth object of the present invention is to provide a method, in accord with the first object of the present invention, the second object of the present invention and the third object of the present invention, which is readily commercially implemented.

In accord with the objects of the present invention, there is provided a method for detecting and monitoring the concentration of oxidizing contamination in an acid bath employing a monitor silicon substrate, and a method for fabrication of said silicon substrate monitor. To practice the invention, there is first provided a surface doped silicon substrate whose electrical sheet resistance is measured. Upon the silicon substrate is formed a silicon oxide dielectric layer to form a monitor silicon substrate. The monitor silicon substrate is then placed in the buffered oxide etch (BOE) acid etch bath to be tested for a period of time. Then the monitor silicon substrate is removed from the etch bath and the electrical sheet resistance measured again. An increase in the electrical sheet resistance of the silicon substrate greater than the standard deviation is a measure of the presence of oxidizing contamination in the acid bath.

The present invention provides a method for monitoring an acid etching bath employed to etch a silicon oxide layers completely from a silicon substrate upon which the silicon oxide layer is formed. A means for implementing the method employs a silicon substrate fabricated in accord with the following procedure: (1) A layer of silicon oxide is formed upon a P-type silicon wafer of between 15 and 25 ohm-centimeter resistivity employing thermal oxidation to a thickness of 250 angstroms; (2) an ion implant employing $AS^{75}$ ions is performed to provide a doped surface layer; (3) a rapid thermal anneal is performed at 1100 degrees centigrade.

The present invention provides a method for measuring the extent of oxidizing contamination in a buffered oxide etch (BOE) acid etching bath of concentration ratio of which is employed to remove completely all silicon oxide surface layers prior to further processing.

The present invention employs methods and materials as are known in the art of silicon integrated circuit microelectronics fabrication, but in a novel and original arrangement. Therefore the present invention is readily commercially implemented.

BRIEF DESCRIPTION OF THE DRAWINGS

The objects, features and advantages of the present invention are understood within the context of the Description of the Preferred Embodiment as set forth below. The Description of the Preferred Embodiment is understood within the context of the accompanying drawings, which form a material part of this disclosure, wherein.

DESCRIPTION OF THE PREFERRED EMBODIMENT

Figure 1:
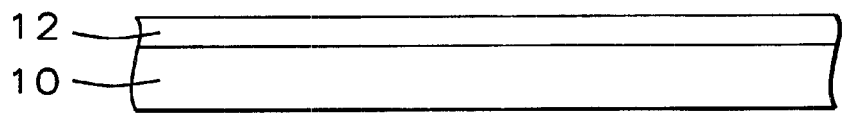
FIG. 1, FIG. 2, FIG. 3 and FIG. 4 are a series of schematic cross-sectional diagrams illustrating the result of performing the method of the invention within the context of the detection of oxidizing contamination such as, for example, hydrogen peroxide in an acid etching bath employed to etch silicon oxide layers formed on silicon substrates.
Figure 2:
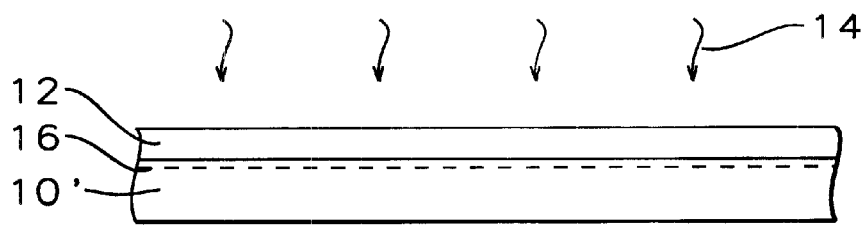
Figure 3:
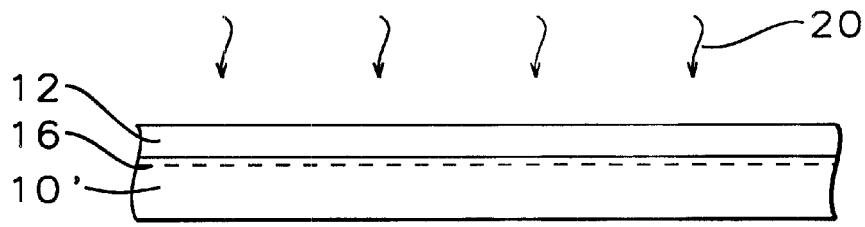
Figure 4:
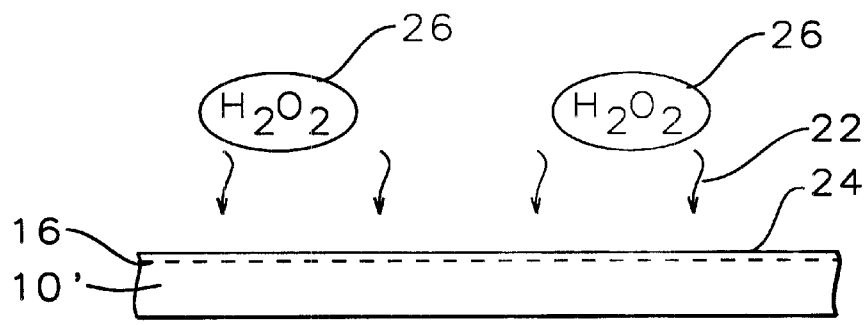

The present invention provides a method for detecting oxidizing contamination in an acid etch bath employed to etch silicon oxide layers formed upon silicon substrates. As a means of implementing the method, a monitor silicon substrate with a doped surface layer providing a known surface electrical sheet resistance having a silicon oxide layer formed thereover is employed. After completely etching away the silicon oxide layer in the acid etch bath being monitored, the electrical sheet resistance is re-measured, whose change is an indication of the degree of oxidizing contaminant present such as, for example, hydrogen peroxide. FIG. 1 to FIG. 3 illustrate the means of implementing the method of the present invention. FIG. 4 illustrates the method of the present invention.

Referring now more particularly to FIG. 1, there is shown a schematic cross-sectional diagram illustrating an early stage in the implementation of the method of the present invention.

Shown in FIG. 1 is a silicon substrate 10 upon which is formed a silicon oxide layer 12. Preferably the silicon substrate 10 is a single crystalline (100) oriented silicon substrate of p-type doping of from about 15 to about 25 ohm-centimeter resistivity.

With respect to the silicon oxide layer 12 shown in FIG. 1, the silicon oxide layer 12 is preferably formed to a thickness of about 250 angstroms employing thermal oxidation at a temperature of about 925 degrees centigrade in an oxidizing environment of oxygen ($O_2$) and hydrogen chloride (HCl) gases for a time of about 35 minutes.

Referring now to FIG. 2, there is shown a schematic cross-sectional diagram illustrating the result of further implementation of the formation of the monitor silicon substrate whose schematic cross-sectional diagram is shown in FIG. 1. Shown in FIG. 2 is a silicon substrate equivalent to the silicon substrate shown in FIG. 1, but where there has been implanted by means of ion implantation 14 a concentration of $As^{75}$ ions into the silicon at the interface between the silicon oxide layer 12 and the silicon substrate 10' to form an implanted ion layer 16.

With respect to the ion implantation 14 shown in FIG. 2, the ion implantation 14 employs the following process conditions: (1) $As^{75}$ ions; (2) accelerating potential 80 keV; (3) ion concentration 1E15; (4) projected range RP 388 angstroms; (5) standard deviation of change in RP of 125 angstroms. Preferably the difference between the projected range RP and the standard deviation, or change, in projected range is about 250 angstroms.

Referring now more particularly to FIG. 3, there is shown a schematic cross-sectional diagram illustrating the results of further processing of the silicon monitor substrate employed as a means of implementing the method of the present invention. Shown in FIG. 3 is a monitor silicon substrate equivalent to the silicon wafer shown in FIG. 2, but where there has been carried out a rapid thermal anneal (RTA) 20.

With respect to the rapid thermal anneal 20 shown in FIG. 3, the rapid thermal anneal (RTA) 20 preferably employs the following process conditions: (1) temperature of about 1100 degrees centigrade; (2) nitrogen gas atmosphere; (3) time 10 seconds. Preferably the surface electrical sheet resistance after the RTA process is 122+/−12 ohm/square.

Referring now more particularly to FIG. 4, there is shown a schematic cross-sectional diagram illustrating the method of the present invention. FIG. 4 illustrates the monitor silicon substrate of FIG. 3 being employed to implement the method of the invention.

Shown in FIG. 4 is the monitor silicon wafer 10' after being etched in an acid etching bath 22 for a period of time to completely remove any silicon oxide layer from the silicon surface 24, exposing the silicon surface 24 to the etching bath 22. Any oxidizing contaminant species 26 will react with the silicon surface 24 in such a fashion as to increase the surface electrical resistance. While not wishing to be bound by any particular hypothesis, it is speculated that an oxidizing contamination such as, for example, hydrogen peroxide ($H_2O_2$) may react with the silicon surface under the conditions of exposure to form silicon oxide according to the chemical reaction:

$$Si+2H_2O_2=SiO_2+2H_2O$$

whereupon the $SiO_2$ formed is etched away immediately by the BOE acid etch bath, leading to the loss of surface silicon having the dopant therein and hence to an increase in electrical resistance.

EXPERIMENTAL

The benefits and advantages of the present invention are exemplified by the experimental data obtained employing silicon monitor substrates determine the effect of hydrogen peroxide contamination in acid etching baths employed to etch the silicon oxide layers from the monitor silicon substrates.

Silicon substrates were prepared according to the following experimental conditions: (1) single crystal (100) silicon substrates with p-type doping from about 15 to about 25 ohm-centimeter resistivity were thermally oxidized in $O_2$/HCl at 920 degrees centigrade for 35 minutes to form silicon oxide layers of about 250 angstroms thickness; (2) ion implantation of $As^{75}$ ions at 80 keV accelerating potential at a concentration of 1E15 ions/square centimeter; (3) rapid thermal anneal at 1100 degrees centigrade for 10 seconds in nitrogen gas; (4) surface electrical sheet resistance measured to be 122+/−12 ohm/square; and (5) projected range RP of $As^{75}$ ions 388 angstroms, with RP standard deviation of 125 angstroms.

Monitor silicon substrates so prepared were dip etched in uncontaminated BOE 50:1 acid etching baths for times of from 2 to 5 minutes and the surface electrical sheet resistances of the etched silicon substrates measured. The results were compared with similar samples etched in BOE 50:1 acid etch baths purposely contaminated with about 100 parts/million (ppm) of hydrogen peroxide. The results are shown below in Table I:

Table I

Sheet Resistance of Monitor Silicon Substrates After Etching in BOE Acid Bath

| Etch Time, Minutes | Sheet Resistance, Ohm/square Uncontaminated BOE | Sheet Resistance, Ohm/square Contaminated BOE |
|---|---|---|
| 2 | 121.43 | 123.42 |
| 3 | 126.12 | 181.71 |
| 4 | 131.33 | 318.42 |
| 5 | 136.12 | 1012.3 |

Figure 5:
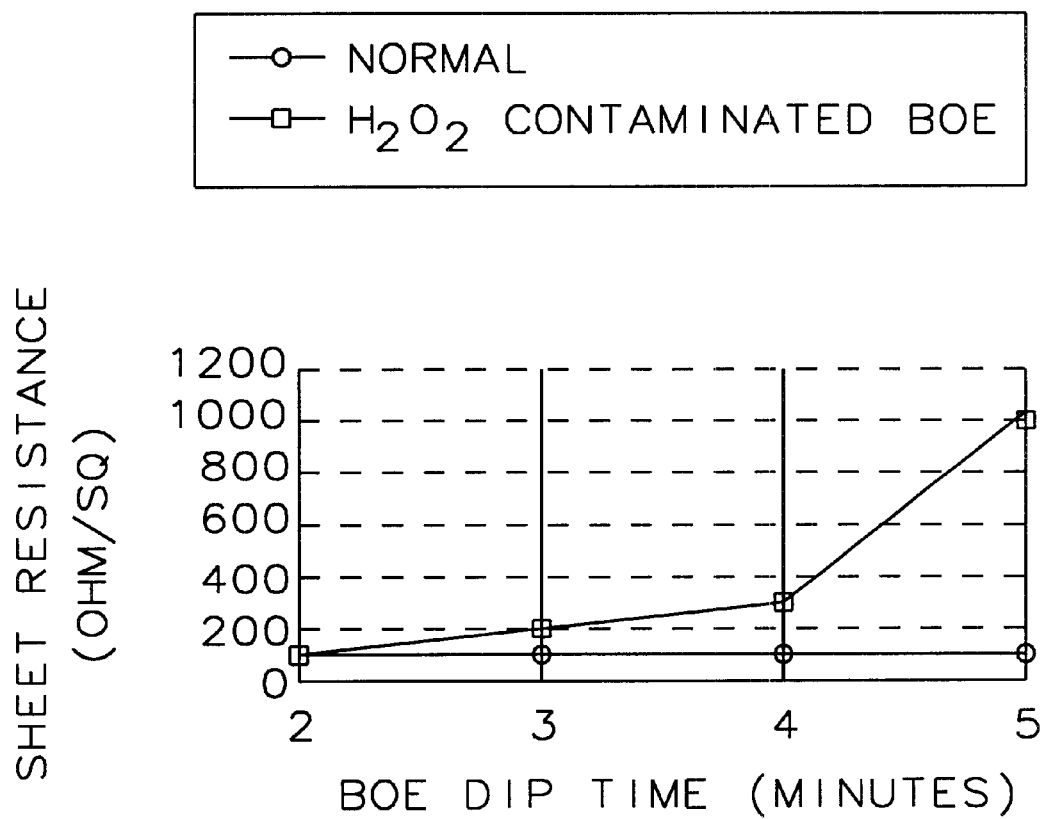
FIG. 5 is a graph of the surface electrical sheet resistance of a surface doped silicon substrate over which is formed a silicon oxide layer versus etching time in the acid bath for normal and contaminated acid etch baths.

The experimental results are also shown in FIG. 5, which gives the resulting surface sheet resistance measurements for etched monitor silicon substrates after etching in uncontaminated and contaminated acid etch baths for 2 to 5 minutes. It is clear that the contaminated bath produces resistance changes directly related to the time of exposure of the silicon substrate surface to the contamination of hydrogen peroxide in the acid etch bath.

The efficacy of the present invention is exemplified by measurements on silicon integrated circuit microelectronics device substrates. For example, after monitoring of BOE acid etch baths to assure that no hydrogen peroxide contamination is present employing the method and means of the present invention, the yield at final test of the particular part number TMI 142 is increased from 81 to 88%.

As is understood by a person skilled in the art, the preferred embodiment of the present invention is illustrative of the invention rather than limiting of the present invention. Revisions and modifications may be made to materials, structures and dimensions through which is provided the preferred embodiment of the present invention while still providing embodiments which are within the spirit and scope of the present invention, as defined by the appended claims.

What is claimed is:

1. A method for detecting hydrogen peroxide contamination in an acid etching bath employed in etching silicon oxide layers formed on silicon substrates comprising:

providing a monitor silicon substrate having a doped surface region of measured electrical sheet resistance over which is formed a silicon oxide layer;

etching the silicon oxide layer away completely in said acid etching bath; and determining the surface electrical sheet resistance change of the monitor silicon substrate correlating to the amount of hydrogen peroxide contamination in the acid bath.

2. The method of claim 1 wherein the monitor silicon substrate is a single crystalline silicon wafer with p-type doping of (100) crystalline orientation having a resistivity of from about 15 to about 25 ohm-centimeter.

3. The method of claim 1 wherein the monitor silicon substrate has a surface doping to provide a initial surface electrical sheet resistance of 122+/−12 ohms per square.

4. The method of claim 1 wherein the surface doping is provided by ion implantation of $As^{75}$ ions at 80 kcV potential.

5. The method of claim 1 wherein said silicon oxide layer is formed employing thermal oxidation of silicon to a thickness of about 250 angstroms.

6. The method of claim 1 wherein the etching time for complete removal of silicon oxide is 3 minutes.

7. The method of claim 1 wherein the acid etching bath is a buffered oxide etch (BOE) etching bath with a concentration ratio of 50:1.

8. The method of claim 7 wherein the specified etch rate of silicon oxide in the BOE acid etch bath is 190+/−20 angstroms per minute.

* * * * *